(12) United States Patent  
Shin

(10) Patent No.: US 7,348,572 B2  
(45) Date of Patent: Mar. 25, 2008

(54) TOOTHBRUSH STERILIZER

(75) Inventor: Choong-sik Shin, Seoul (KR)

(73) Assignee: Esencia Co., Ltd., Seoul (KR)

( * ) Notice: Subject to any disclaimer, the term of this patent is extended or adjusted under 35 U.S.C. 154(b) by 59 days.

(21) Appl. No.: 11/362,948

(22) Filed: Feb. 28, 2006

(65) Prior Publication Data

US 2007/0200072 A1 Aug. 30, 2007

(51) Int. Cl.  
*A61L 2/10* (2006.01)

(52) U.S. Cl. .............. 250/455.11; 250/461.1; 250/504 H; 422/24

(58) Field of Classification Search .......... None  
See application file for complete search history.

(56) References Cited

U.S. PATENT DOCUMENTS

| | | | | |
|---|---|---|---|---|
| 5,487,877 A | * | 1/1996 | Choi | 422/300 |
| D501,930 S | * | 2/2005 | Shin | D24/217 |
| D502,266 S | * | 2/2005 | Shin | D24/217 |
| D502,546 S | * | 3/2005 | Shin | D24/217 |
| D542,929 S | * | 5/2007 | Shin | D24/217 |
| D542,930 S | * | 5/2007 | Shin | D24/217 |
| 2006/0029518 A1 | * | 2/2006 | Yu | 422/62 |

* cited by examiner

*Primary Examiner*—Nikita Wells  
(74) *Attorney, Agent, or Firm*—Rabin & Berdo, PC

(57) ABSTRACT

A portable toothbrush sterilizer is provided. The portable toothbrush sterilizer includes a lower case (100*a*), an upper case (200*a*), a protective cap (500), and a cover (300*a*). The lower case (100*a*) has a sterilizer compartment (150) and a battery compartment (140). The upper case (200*a*) is coupled above the lower case (100*a*) and includes a storage space (210) and a switch hole (250) with a touch switch (164) therein. The storage space (210) has a toothbrush bristle compartment (212) with an ultraviolet ray emitting hole (240) formed on a side thereof and a toothbrush handle compartment (214). The protective cap (500) is detachably attached to the toothbrush bristle compartment (212) and includes a second ultraviolet ray emitting hole (510) and an open portion (550). The cover 300*a* is disposed above the upper case (200*a*) and includes a button (340) for pressing the touch switch (164).

15 Claims, 14 Drawing Sheets

TOOTHBRUSH STERILIZER

BACKGROUND OF THE INVENTION

1. Field of the Invention

The present invention relates to a portable toothbrush sterilizer, and more particularly, to a portable toothbrush sterilizer that allows easy storage of toothbrushes, increases the sterilizing effectiveness of a sterilizing lamp, and provides an aesthetically pleasing design that can be varied and does not discolor, for a long service life.

2. Description of the Related Art

For the hygienic storage of toothbrushes, a portable toothbrush sterilizer uses a built-in sterilizing lamp to sterilize the bristles of a single toothbrush stored in the sterilizer.

FIG. 1 is an exploded perspective view of a toothbrush sterilizer according to the related art, FIG. 2 is a longitudinal sectional view of a toothbrush sterilizer according to the related art, and FIG. 3 is a transverse sectional view of a toothbrush sterilizer according to the related art. Referring to FIGS. 1 through 3, a toothbrush sterilizer 10 according to the related art includes a lower case 100, an upper case 200 provided above the lower case 100, and a cover 300 that opens and closes the top of the upper case 200.

The lower case 100 has a floor 110 and a peripheral wall 120 extending a predetermined height from the periphery of the floor 110. A mounting hole 112 is formed through the upper central portion of the floor 110.

Levering tabs 122 extend horizontally from the central portion at the front of the peripheral wall 120, and a hinge protrusion 130 protrudes respectively from each rear side of the peripheral wall 120.

Also, a battery compartment 140 with an opening and closing plate is formed at the rear of the floor 110 in order to store a portable battery, and a sterilizer compartment 150 for storing a sterilizer 160 having a sterilizing lamp 162 and a touch switch 164 is formed on the opposite side to the battery compartment 140.

Here, when the touch switch 164 is pressed to transmit an ON signal, a circuit, that allows the sterilizer 160 to receive current from the portable battery and transmit it to the sterilizing lamp 162 to activate the lamp, is included in the related art; and therefore a detailed explanation of this circuit will be omitted herein. When the pressure on the touch switch 164 is removed to transmit an OFF signal through the circuit, the current from the portable battery to the sterilizing lamp 162 is blocked to turn the lamp off.

The upper case 200 includes an upper surface 220 and a peripheral wall 230 extending downwards from the periphery of the upper surface 220, and a catch 260 protruding from a central front portion of the peripheral wall 230.

The upper surface 220 is recessed downward to form a storage space 210 for storing a toothbrush 400. The storage space 210 has toothbrush bristle compartment 212 for storing the toothbrush bristles 410 and a toothbrush handle compartment 214 for storing the toothbrush handle 420 that extends from the toothbrush bristle compartment 212.

An ultraviolet ray emitting hole 240, through which the sterilizing lamp 162 emits ultraviolet rays, is formed at the rear of the toothbrush bristle compartment 212.

To prevent movement of the toothbrush 400 within the storage space 210, a holding member 219 is provided between the toothbrush bristle compartment 212 and the toothbrush handle compartment 214. The cover 300 includes a hinge hole 310 formed in either side at its rear, a ventilating hole 320 formed in a portion of its top surface, an opening tab 330 extending horizontally from the front central portion thereof, and a catch hole 350 formed in its inner surface for coupling with the catch 260.

Furthermore, the cover 300 includes a button 340 formed on the inside of the cover corresponding in position to the touch switch 164, to press the switch through a switch hole 250.

In the coupling structure of the above toothbrush sterilizer 10, the upper case 200 is seated on and fixed above the lower case 100 containing the portable battery and sterilizer 160, the hinge hole 310 has the hinge protrusion 130 (protruding from either side of the lower case 100) inserted therein to form a hinge, and the cover 300 pivots up and down around the hinge protrusion 130 to open and close the top of the upper case 200.

The toothbrush sterilizer with the above coupling structure is used in the following way.

First, in order to pivot the cover 300 to open the top of the upper case 200, a user grasps the levering tab 122 on the lower case 100 with one hand and grasps and lifts the opening tab 330 with the other hand.

The pivoting force causes the catch hole 350 of the cover 300 to detach from the catch 260 of the upper case 200, and when the cover 300 is continuously pivoted around the hinge protrusion 130, the top of the upper case 200 is opened.

A toothbrush 400 can then be inserted in or remove from the storage space 210 through the top of the open upper case 200.

To close the top of the open upper case 200, the cover 300 can be pivoted in the opposite direction, so that the pivoting force pivots the cover 300 around the hinge protrusion 130, thus closing the top of the upper case 200.

The button 340 that is formed on the inner surface of the closing cover 300 presses the touch switch 164 (a part of which protrudes from the switch hole 250 in the upper case 200).

The pressed touch switch 164 prompts the sterilizer 160 to receive a current from the portable battery and activate the sterilizing lamp 162, so that ultraviolet rays emitted from the sterilizing lamp 162 pass through the ultraviolet ray emitting hole 240 to sterilize the inside of the toothbrush bristle compartment 212. The sterilizing lamp 162 operates only for a predetermined duration.

In this way, the toothbrush bristles 410 of the toothbrush 400 stored in the storage space 210 are sterilized.

However, a used toothbrush 400, especially its bristles, have a lot of moisture containing remaining toothpaste ingredients, so that when such a toothbrush 400 is stored in the storage space 210 of the toothbrush sterilizer 10, the moisture on the bristles collects on the floor of the toothbrush bristle compartment 212. The collected moisture partially evaporates due to the heat generated by the sterilizing lamp 162. The remaining moisture is either chemically deposited on the floor of the toothbrush bristle compartment 212, or drains down to be toothbrush handle compartment 214, where it is deposited.

Accordingly, after a long period of use, the floors of the toothbrush bristle compartment 212 and the toothbrush handle compartment 214 are contaminated by residual moisture, resulting in reduced sterilizing effectiveness.

Furthermore, to wash the contaminated portions, the entire sterilizer must be washed with water or other cleaning agent. During this washing process, if washing liquid comes into direct contact with the sterilizing lamp, and more specifically, if it leaks through the ultraviolet ray emitting hole and comes into contact with the sterilizer and portable battery in the lower case, the toothbrush sterilizer will most likely be rendered inoperable.

Also, there is the problem of the interior of the toothbrush bristle compartment becoming discolored by exposure to the ultraviolet rays-emitted from the sterilizing lamp. That is, the moisture containing toothpaste remnants that collects in the toothbrush bristle compartment chemically reacts when exposed to the emitted ultraviolet rays, and discolors the toothbrush bristle compartment when combined with other factors, so that the evident discoloration reduces product value.

Another problem occurs when a stored toothbrush and a sterilizing lamp are placed too close together by a careless user or by a shock, so that a portion of the toothbrush's bristles come into contact with the surface of the sterilizing lamp. Here, the powered sterilizing lamp generates heat, while the moist bristles contact and cool a portion of the heated lamp, resulting in damage to the lamp due to a temperature discrepancy.

A further problem is that both hands must be used to open the cover in the structure employing the catch on the upper case that catches in the catch hole on the cover. While one hand grasps the levering tab, the other must grasp the opening tab to lift open the cover.

The protruding lengths of the levering tab and the opening tab also present a problem. If the lengths are short, then grasping force thereof is reduced due to slippage during grasping of the short protrusions, thereby limiting the pivoting force and easy opening of the cover.

Should the protruding lengths of the tabs be lengthened, they can easily be damaged from shocks. Also, lengthening the tabs will compromise the outward appearance of the product to reduce its market competitiveness.

While the touch switch is activated by a portion thereof that protrudes through the switch hole being pressed by the button on the cover, the button can press the touch switch to activate the sterilizing lamp, when the cover is not properly closed. In this case, potentially harmful ultraviolet rays are emitted outside of the toothbrush sterilizer.

Furthermore, while the cover is open, the touch switch protruding through the switch hole in the upper case can be pressed by anyone, including curious children, who may suffer injury from exposure to the ultraviolet rays emitted by the sterilizing lamp.

SUMMARY OF THE INVENTION

An object of the present invention is to provide a portable toothbrush sterilizer with a detachable protective cap in a toothbrush bristle compartment for maintaining a clean environment and enabling easy cleaning, in order for a long product life and the prevention of discoloration.

Another object of the present invention is to provide a portable toothbrush sterilizer with a boundary formed at the open portion of the protective cap to prevent moisture collected on the floor of the protective cap from flowing into the handle compartment to minimize contamination of the latter.

A further object of the present invention is to provide a portable toothbrush sterilizer with a plurality of drain holes formed on the floors of the upper case and the protective cap, so that moisture collected on the floor of the protective cap can be drained to the outside in order to minimize contamination of the floor of the protective cap.

A still further object of the present invention is to provide a portable toothbrush sterilizer that allows the pivoting force of the pivoting member to easily unhook the hooked protrusion from the hooked tab to open the cover, in order to increase user-friendliness.

An even further object of the present invention is to provide a portable toothbrush sterilizer that negates the need for a levering tab and an opening tab with predetermined protruding lengths, so that the design of the portable toothbrush sterilizer, and resultantly, its market competitiveness are improved.

An additional object of the present invention is to provide a portable toothbrush sterilizer that has its touch switch within and not protruding from the switch hole of the upper case, in order to prevent accidental activating of the touch switch, and to activate the touch switch for illuminating the sterilizing lamp only when the cover is closed, thereby preventing burns.

A further additional object of the present invention is to provide a portable toothbrush sterilizer that has at least one support for elevating the bristles of a toothbrush a predetermined height from the floor of the toothbrush bristle compartment, so that the moisture on the bristles dries quickly for better sterilizing ability.

A still further additional object of the present invention is to provide a portable toothbrush sterilizer having a semi-transparent window on the top surface of the cover and an adjacent reflector, so that light from the ultraviolet lamp penetrates the semi-transparent window for an aesthetically pleasing effect and the reflector increases the functionality of the product.

An even further additional object of the present invention is to provide a portable toothbrush sterilizer with a third drain hole formed in the toothbrush handle compartment in order to drain moisture on the handle or moisture that flows into the handle compartment.

According to an aspect of the present invention, there is provided a portable toothbrush sterilizer including: a lower case including a sterilizer compartment for storing a sterilizer with a sterilizing lamp and a touch switch, and a batter compartment on a side of the sterilizer compartment; an upper case coupled above the lower case and including: a storage space recessed downward from an upper surface of the upper case for storing a toothbrush, the storage space having: a toothbrush bristle compartment for storing toothbrush bristles of a toothbrush and having an ultraviolet ray emitting hole formed on a side thereof, and a toothbrush handle compartment formed beside the toothbrush bristle compartment for storing a toothbrush handle; and a switch hole formed on a side of an upper surface or a peripheral wall of the upper case and having a touch switch inserted and protruding therein; a protective cap detachably attached to the toothbrush bristle compartment of the upper case and including a second ultraviolet ray emitting hole formed at a side thereof, and an open portion formed at another side thereof for allowing storage of the toothbrush handle; and a pivotably opening and closing cover disposed above the upper case and including a button formed on an inner side thereof for pressing the touch switch.

The protective cap may further include a floor having one or more of a second support rising a predetermined height from the floor, the second support may be a double incline formed with either end thereof inclining a predetermined height, and the second support may be a single incline declining from a side of the second ultraviolet ray emitting hole to an opposite side.

The open portion of the protective cap may form a boundary rising a predetermined height.

The lower case may further include a floor having at least one mounting hole formed therein, the storage space of the upper case may have a plurality of drain holes formed therein, and the floor of the protective cap may have a plurality of second drain holes.

The lower case may include a hollow portion formed at a front central portion thereof; the upper case (200a) may include a hollow portion formed at a front central portion thereof; the hollow portion may have a pivoting protrusion respectively protruding from either end thereof and a hooked tab formed therebehind; the cover may include a hooked protrusion extending downward from a frontal inside center portion thereof for hooking with the hooked tab, and a supporting section formed respectively on either side of the hooked protrusion; the portable toothbrush further may include a pivoting member disposed in the hollow portion of the lower case and the hollow portion of the upper case; the pivoting member may have a horizontal bar with an inserting space formed at a center thereof for preventing interference of the hooked tab and the hooked protrusion, a vertical bar vertically disposed at a front of the horizontal bar, and a hinge hole formed at either side of the horizontal bar and vertical bar with one side of the hinge hole open for inserting the pivoting protrusion of the upper case therein.

The touch switch of the sterilizer may be formed in a length that does not protrude from the switch hole of the upper case.

The cover may be formed partially or entirely of a semi-transparent material, and the cover may include a reflector formed on an upper surface thereof.

The storage space of the upper case may have a fixing hole formed through a floor thereof, and further include a holder with an end thereof inserted and fixed in the fixing hole for allowing easy holding of the toothbrush handle, the holder may include a holding part formed to rise at either side for forming a central inserting space and have a slant toward one side, and a fixing part formed at a bottom of the holder for inserting and fixing in the fixing hole.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
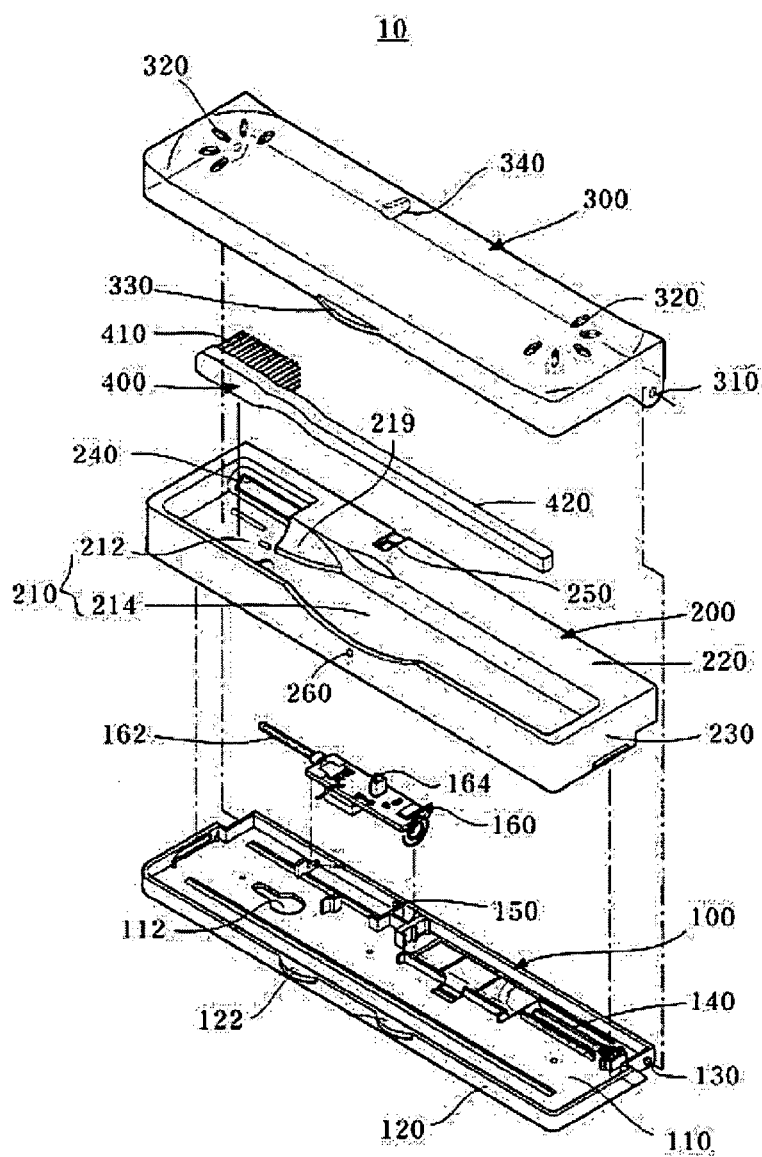
FIG. 1 is an exploded perspective view of a toothbrush sterilizer according to the related art.
Figure 2:
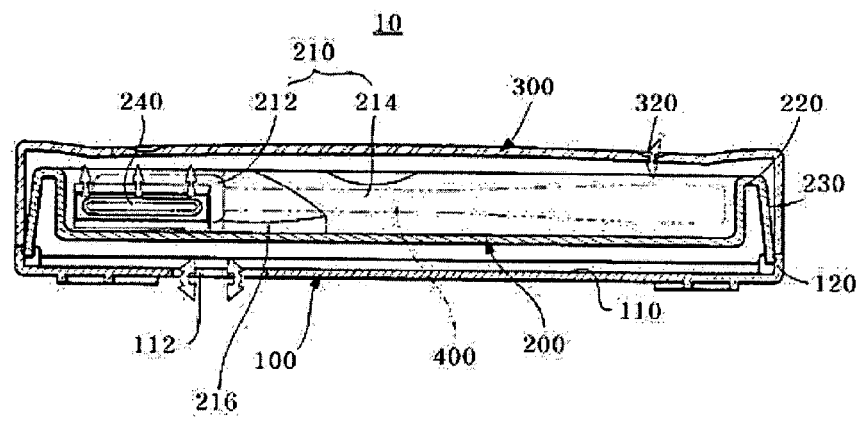
FIG. 2 is a longitudinal sectional view of a toothbrush sterilizer according to the related art.
Figure 3:
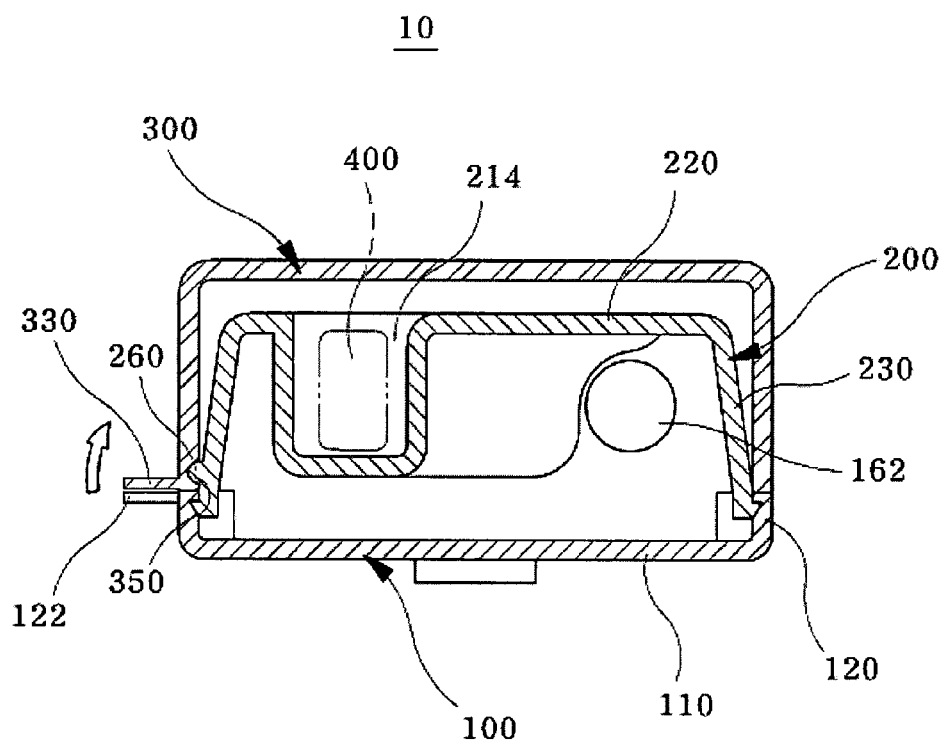
FIG. 3 is a transverse sectional view of a toothbrush sterilizer according to the related art.
Figure 4:
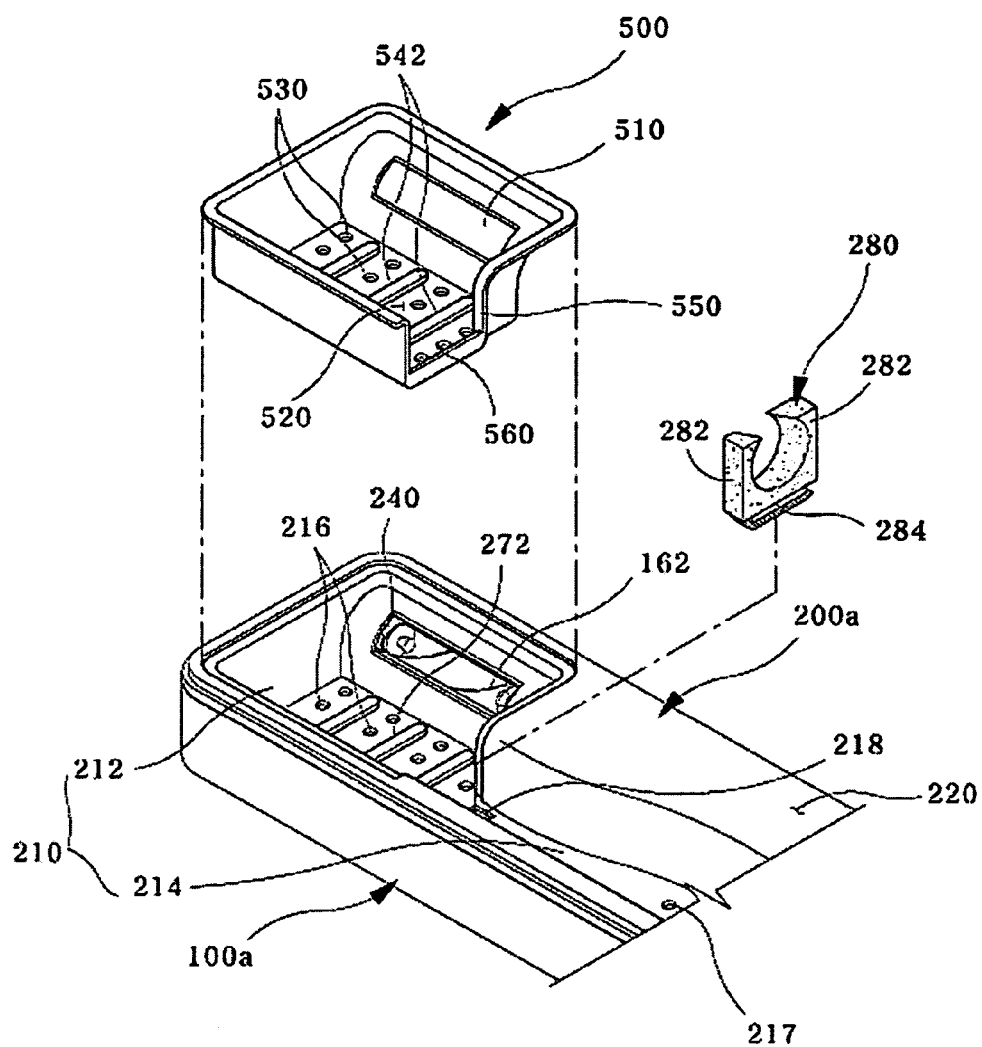
FIG. 4 is an enlarged, exploded view of a portion of a portable toothbrush sterilizer according to the present invention showing a disassembled protective cap.
Figure 5:
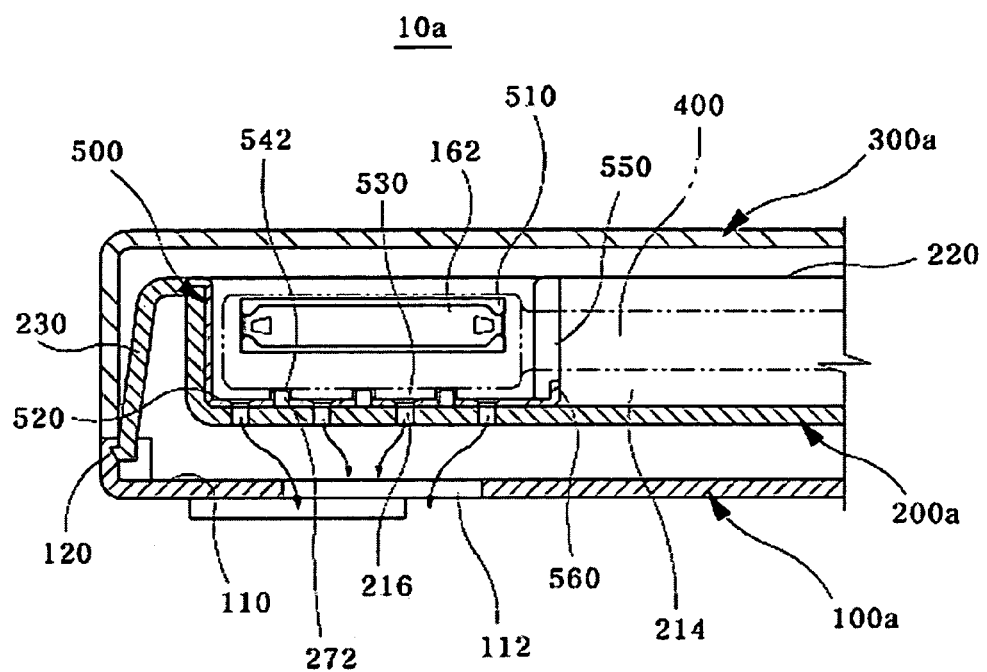
FIG. 5 is a longitudinal sectional view of a portion of a portable toothbrush sterilizer according to the present invention showing an installed protective cap.
Figure 6:
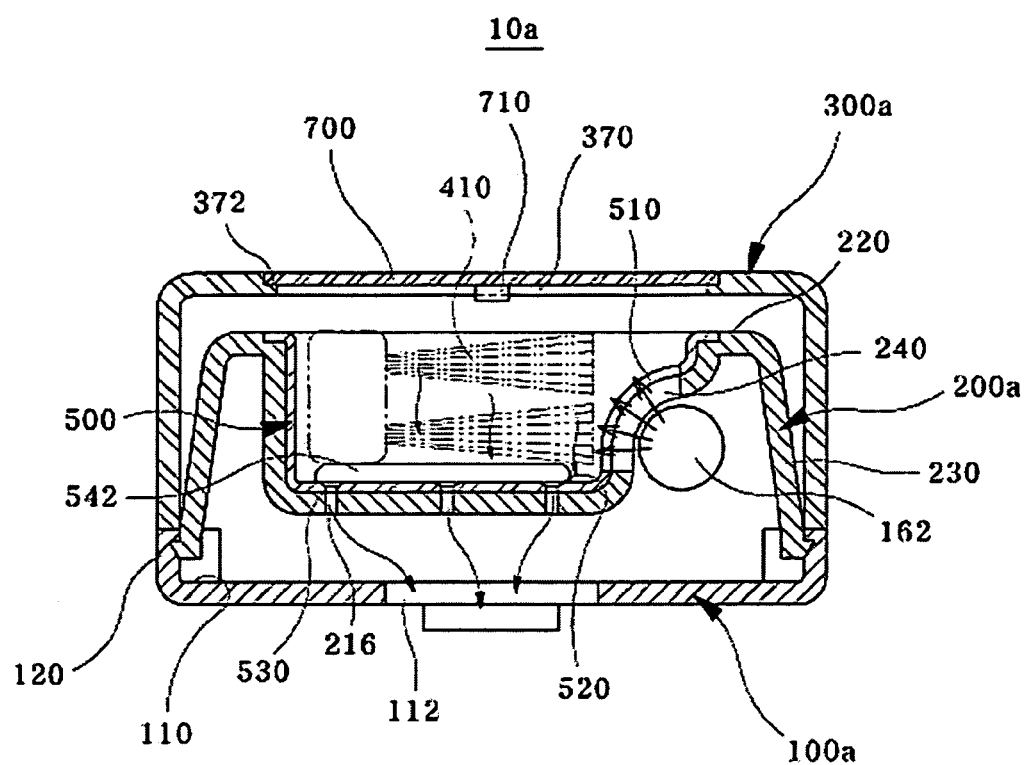
FIG. 6 is a transverse sectional view of a portable toothbrush sterilizer according to the present invention showing an installed protective cap.
Figure 7:
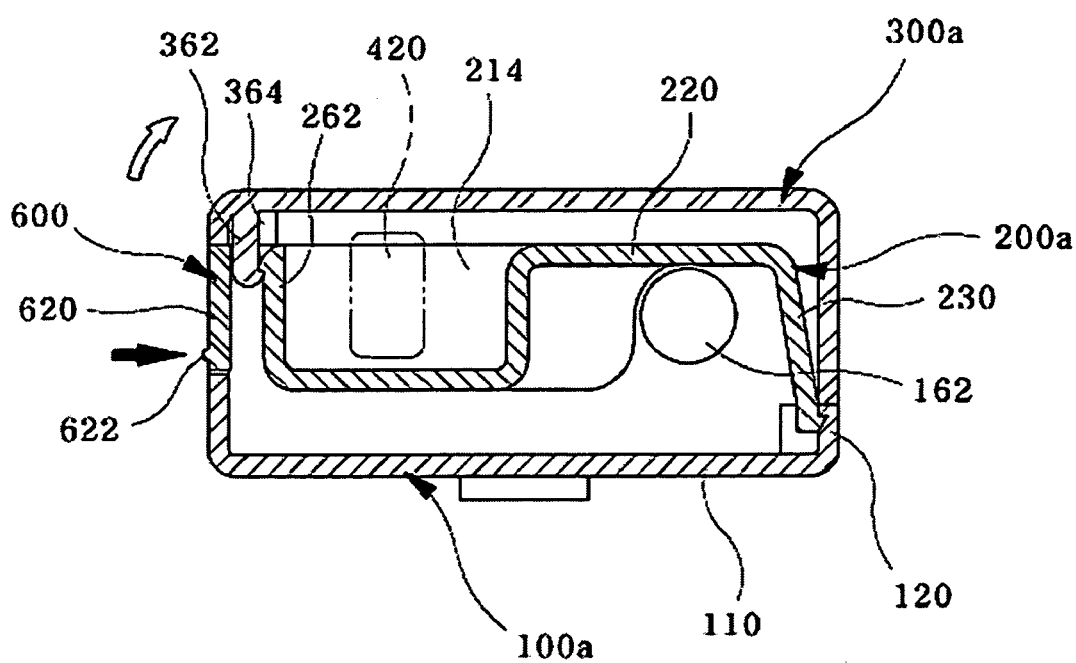
FIG. 7 is a transverse sectional view of the middle portion of a portable toothbrush sterilizer according to the present invention.
Figure 8:
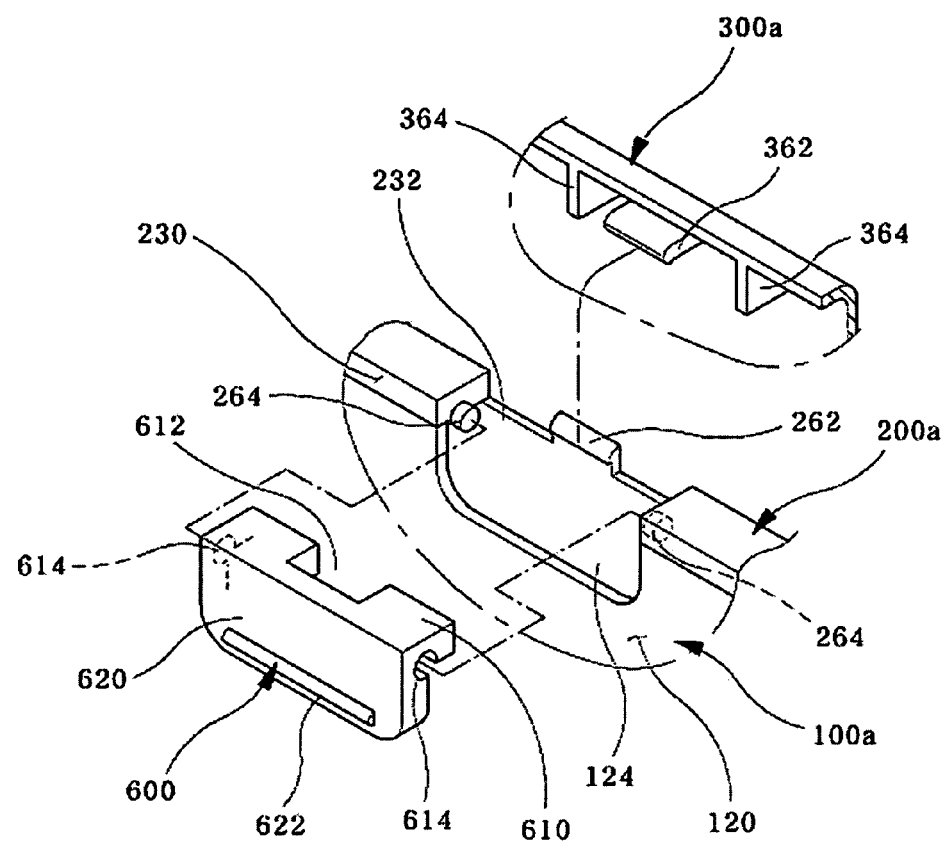
FIG. 8 is an enlarged, exploded perspective view showing a button assembly on a portable toothbrush sterilizer according to the present invention.
Figure 9A:
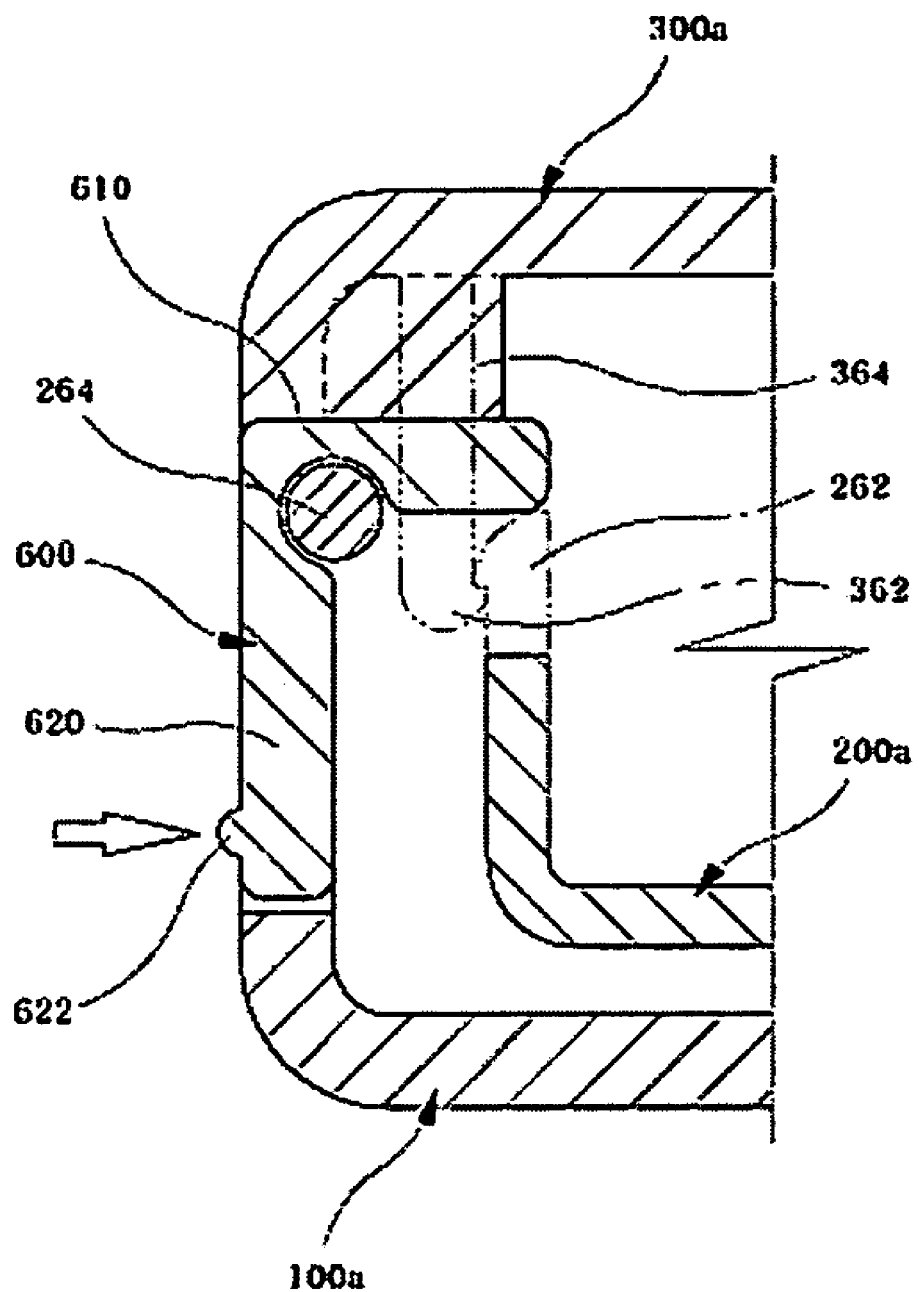
FIG. 9A is a sectional view showing the button assembly in FIG. 7 in a closed position.
Figure 9B:
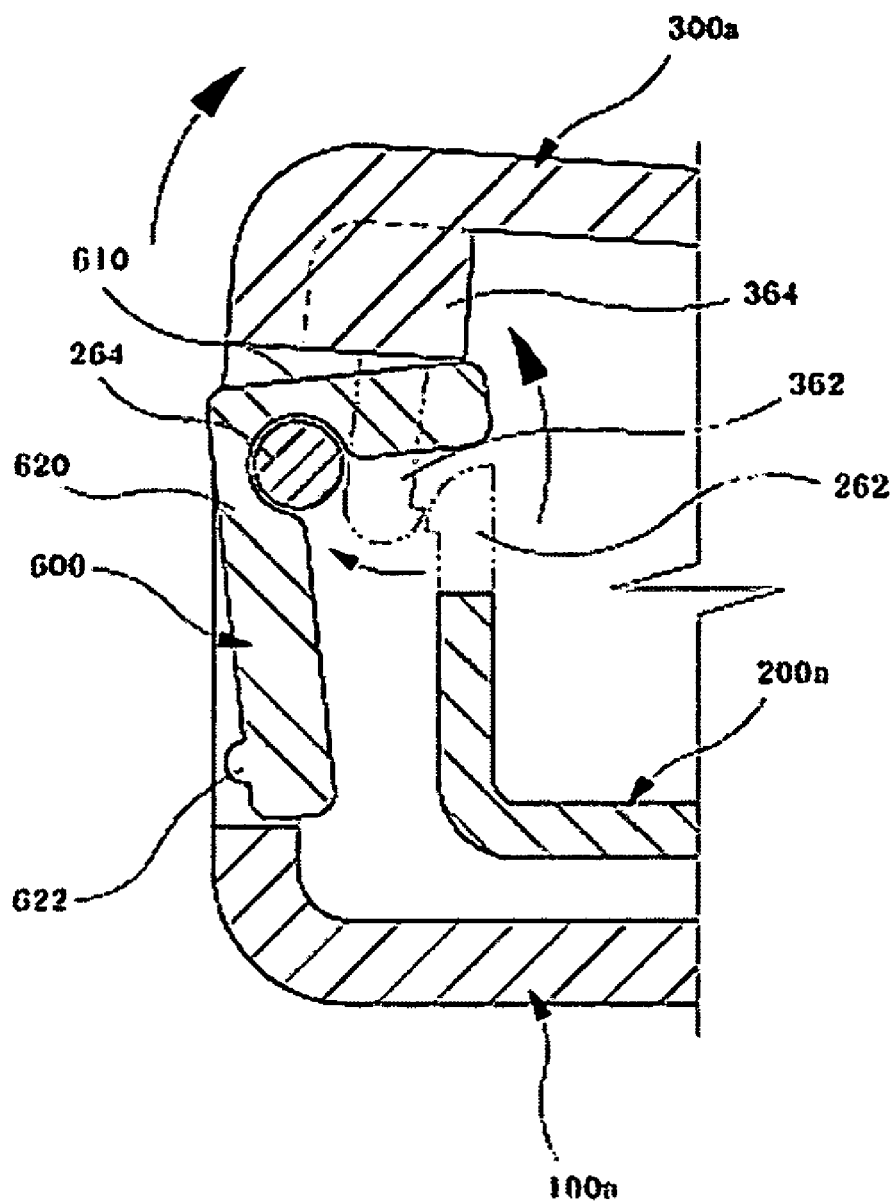
FIG. 9B is a sectional view showing the button assembly in FIG. 7 in an open position.
Figure 10:
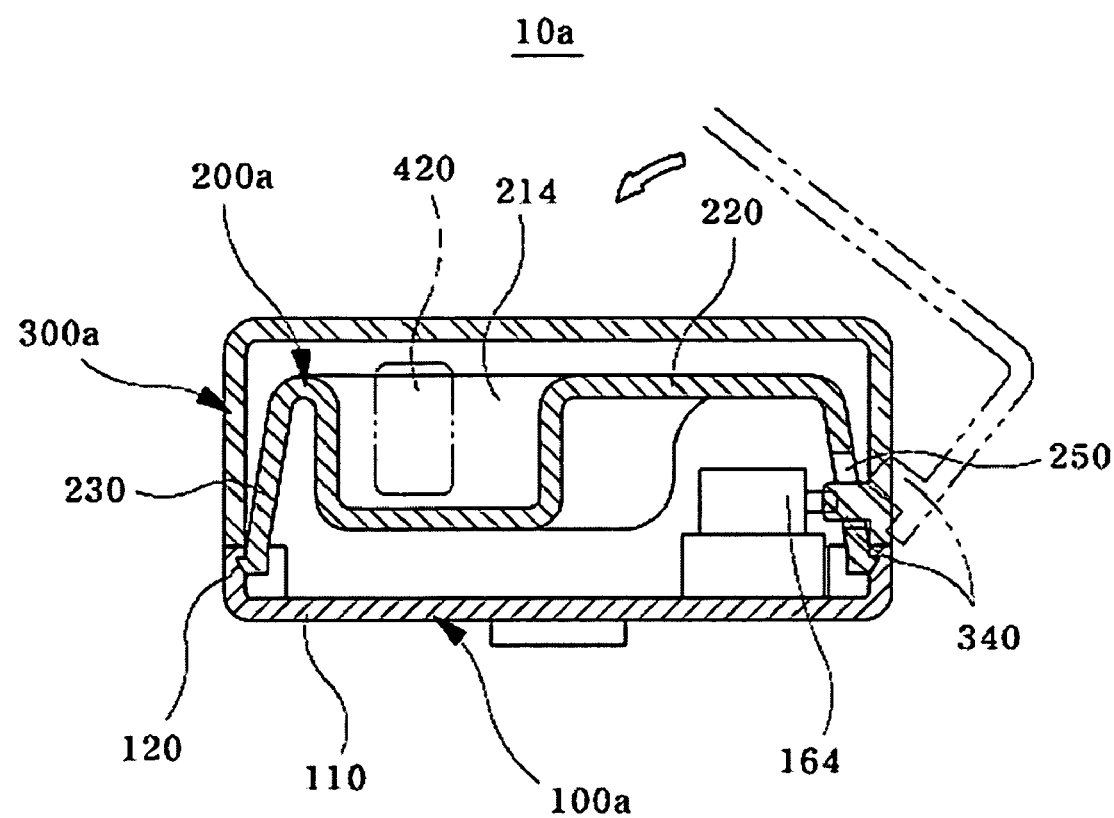
FIG. 10 is a sectional view showing the pressing of a touch switch when a cover of a portable toothbrush sterilizer according to the present invention is opened or closed.
Figure 11A:
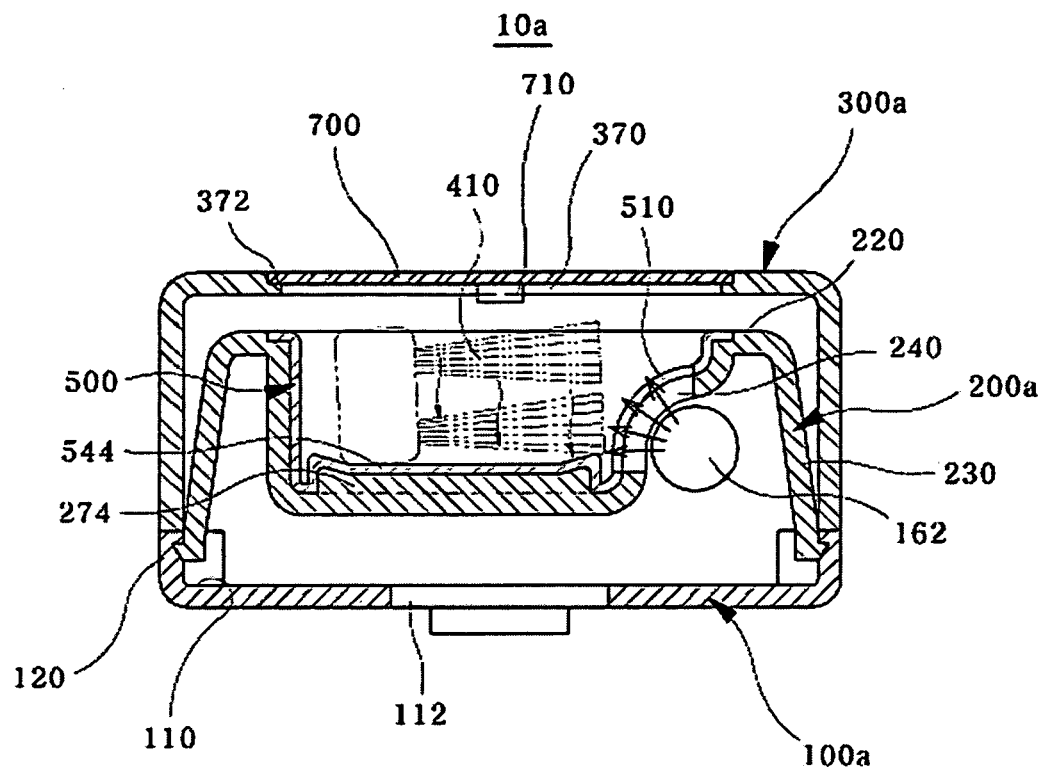
FIG. 11A is a transverse sectional view of a portable toothbrush sterilizer showing a toothbrush rest with both ends protruding.
Figure 11B:
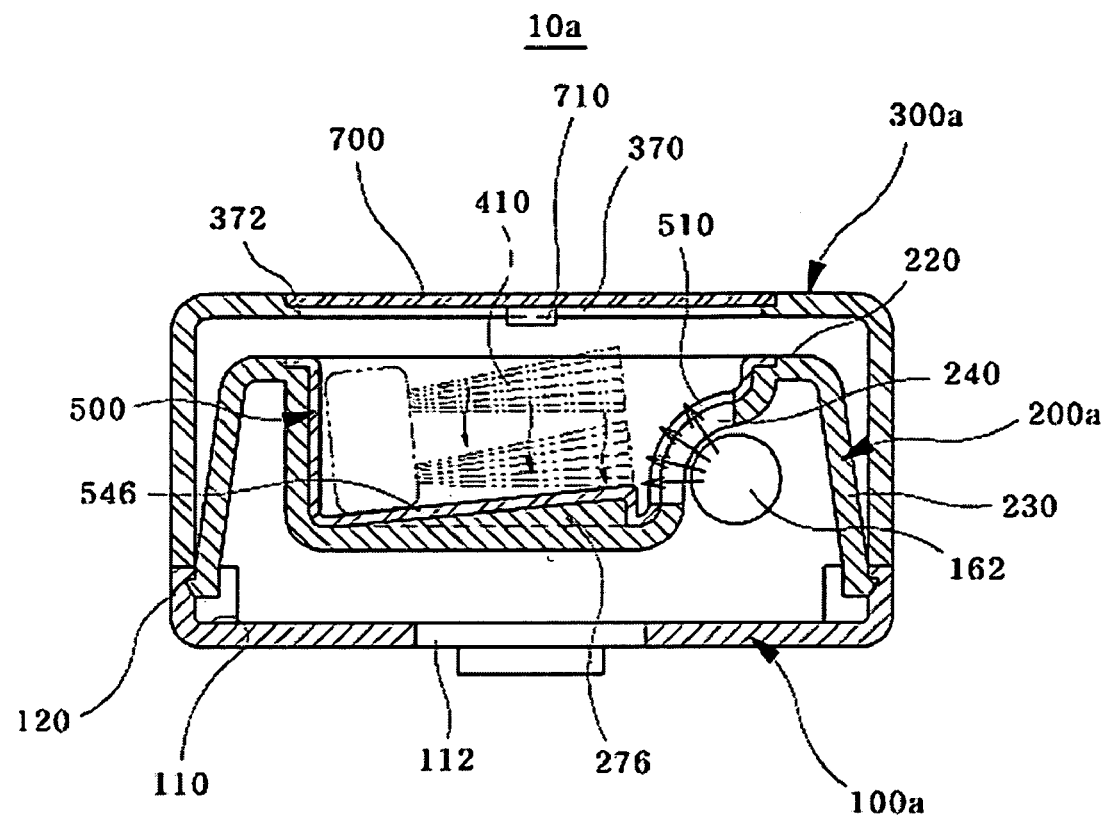
FIG. 11B is a transverse sectional view of a portable toothbrush sterilizer showing an inclining toothbrush stand.
Figure 12:
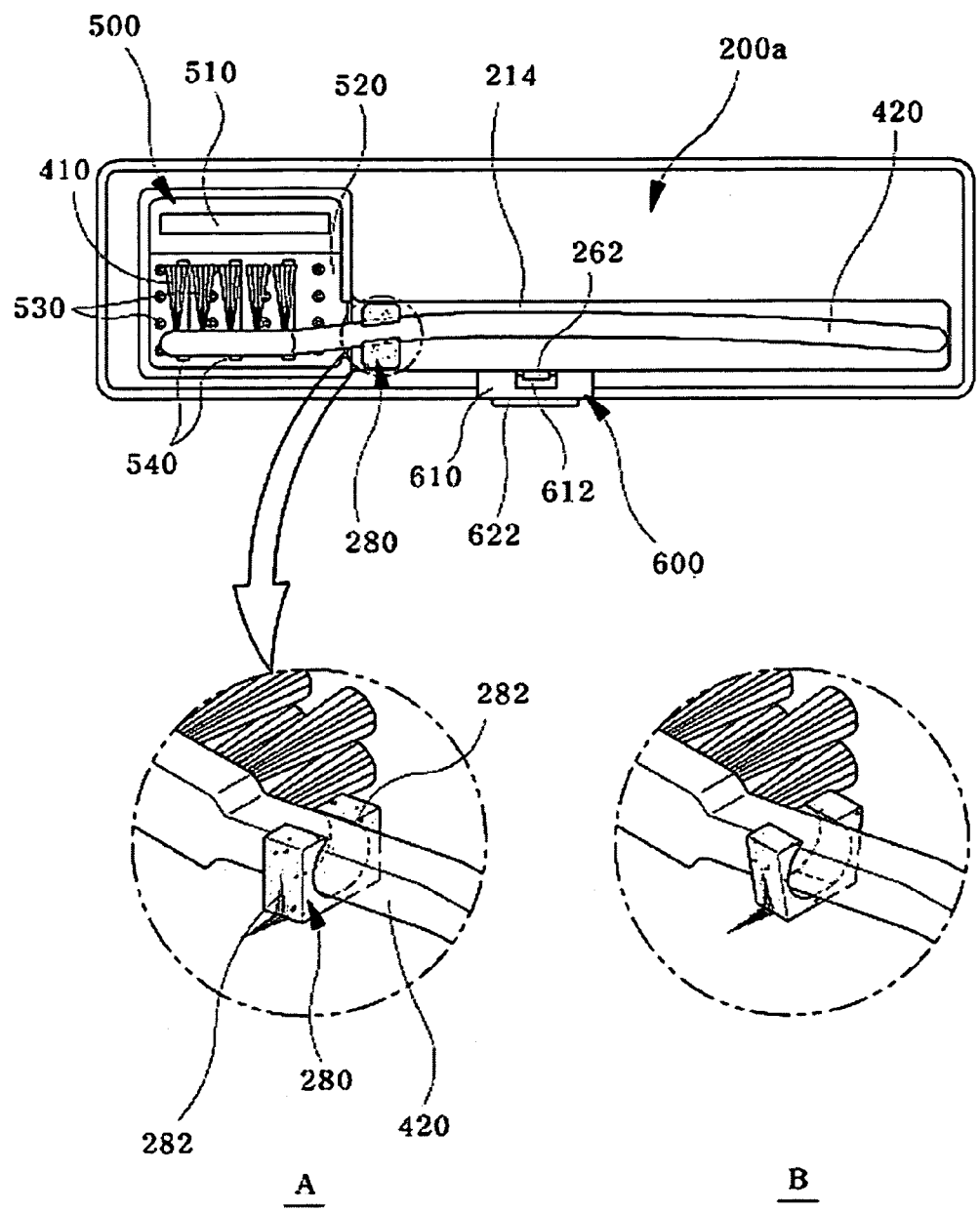
FIG. 12 is a plan view showing a toothbrush inserted into a storage compartment of an upper case of a portable toothbrush sterilizer according to the present invention.
Figure 13:
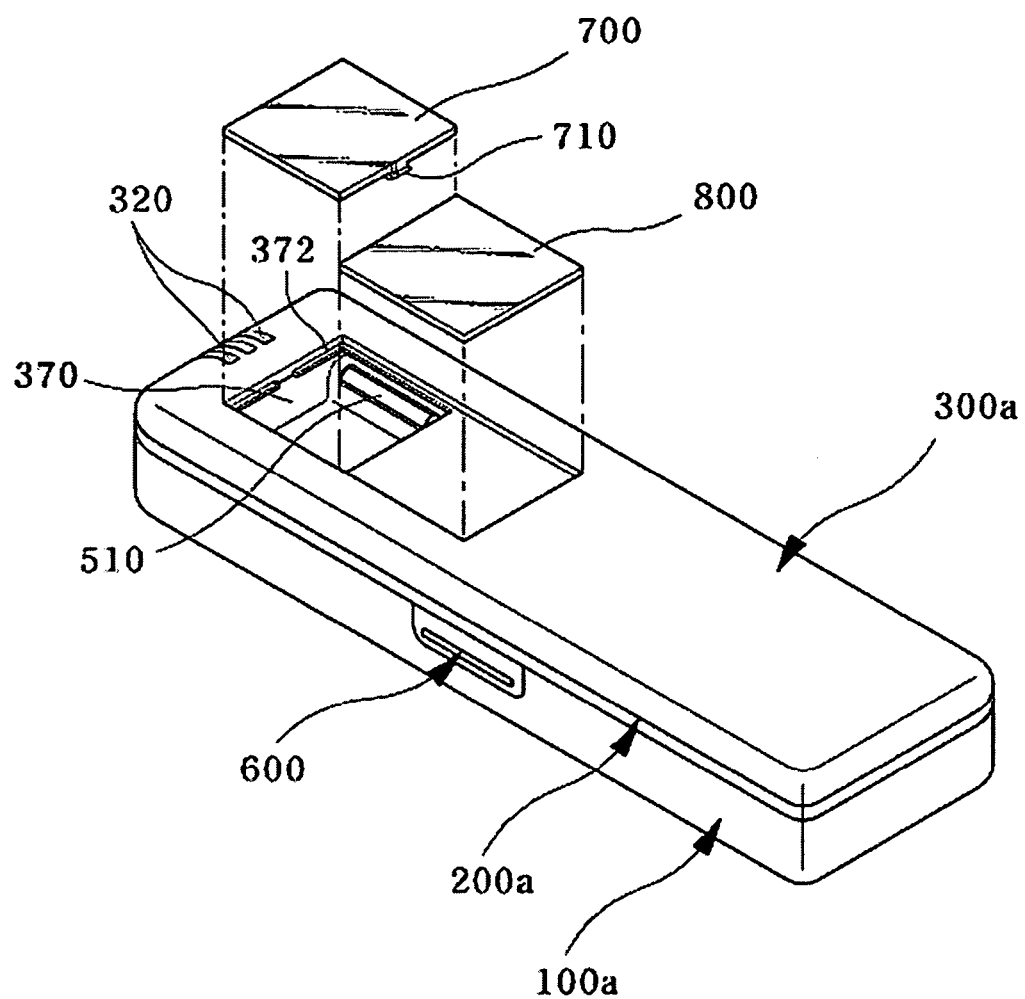
FIG. 13 is an exploded perspective view showing a transparent window and reflector removed from a portable toothbrush sterilizer according to the present invention.

FIG. 4 is an enlarged, exploded view of a portion of a portable toothbrush sterilizer according to the present invention showing a disassembled protective cap; FIG. 5 is a longitudinal sectional view of a portion of a portable toothbrush sterilizer according to the present invention showing an installed protective cap; FIG. 6 is a transverse sectional view of a portable toothbrush sterilizer according to the present invention showing an installed protective cap; FIG. 7 is a transverse sectional view of the middle portion of a portable toothbrush sterilizer according to the present invention; FIG. 8 is an enlarged, exploded perspective view showing a button assembly on a portable toothbrush sterilizer according to the present invention; FIG. 9A is a sectional view showing the button assembly in FIG. 7 in a closed position; FIG. 9B is a sectional view showing the button assembly in FIG. 7 in an open position; FIG. 10 is a sectional view showing the pressing of a touch switch when a cover of a portable toothbrush sterilizer according to the present invention is opened or closed; FIG. 11A is a transverse sectional view of a portable toothbrush sterilizer showing a toothbrush rest with both ends protruding; FIG. 11B is a transverse sectional view of a portable toothbrush sterilizer showing an inclining toothbrush stand; FIG. 12 is a plan view showing a toothbrush inserted into a storage compartment of an upper case of a portable toothbrush sterilizer according to the present invention; and FIG. 13 is an exploded perspective view showing a transparent window and reflector removed from a portable toothbrush sterilizer according to the present invention.

The toothbrush sterilizer 10a includes a lower case 100a with a sterilizer 160 and portable battery within, an upper case 200a coupled above the lower case 100a and forming a storage space 210, and a cover 300a provided above the upper case 200a to open and close.

The lower case 100a includes a floor 110, a peripheral wall 120 rising from the periphery of the floor 110, a battery compartment 140 for storing a portable battery and disposed below the inner rear portion of the lower case 100a, and a sterilizer compartment 150 for storing a sterilizer 160 having a sterilizing lamp 162 and a touch switch 164 formed adjacent to the battery compartment 140. The touch switch 164 of the sterilizer 160 may have a length that prevents it from protruding out from the switch hole 250 of the upper case 200a when the upper case 200a is assembled.

Also, a mounting hole 112 is formed through a central upper portion of the floor 110, and (when referring to FIG. 8) a hollow portion 124 is formed centrally at the front of the peripheral wall 120 for a pivoting member to insert therein.

Of course, a hinge protrusion is formed on either side at the rear of the lower case 10a.

The upper case 200a includes an upper surface 220 and a peripheral wall 230 extending downward from the periphery of the upper surface 220, a storage space 210 recessed downward into the upper surface 220, and a switch hole 250 formed through the portion of the upper surface 220 or peripheral wall 230 where the touch switch 164 is located.

The storage space 210 has a toothbrush bristle compartment 212 for storing a toothbrushes head and bristles 410 and a toothbrush handle compartment 214 disposed below the toothbrush bristle compartment 212 for storing the toothbrush's handle 420.

Also, an ultraviolet ray emitting hole 240 is formed at the rear, that is, the side facing the stored bristles 410, for emitting ultraviolet rays from the sterilizing lamp 162 into the toothbrush bristle compartment 212.

Referring to FIG. 8, the front central portion of the peripheral wall 230 has a hollow portion 232 to locate a pivoting member in. A pivoting protrusion 264 protrudes respectively from either side of the hollow portion 232, and a hooked tab 262 is formed centrally to the rear of the pivoting protrusions 264.

Referring to FIG. 4, the floor of the toothbrush bristle compartment 212 includes a plurality of drain holes 216 and at least one support for supporting the toothbrush bristles 410 and handle 420.

The support may selectively employ a ridge 272 that raises the toothbrush bristles 410 a predetermined distance from the floor, and (as shown in FIGS. 11A and 11B) a double incline 274 inclining symmetrically a predetermined height from both ends of the support and a single incline 276 inclining in the direction from the toothbrush handle 420 to its bristles 410.

When a toothbrush's bristles 410 are stored in the toothbrush bristle compartment 212, the support maintains the bristles 410 a predetermined distance from the floor (to prevent moisture collected on the floor from contacting the bristles 410 for quick drying of the bristles 410) and also positions the bristles 410 in line with the sterilizing lamp 162 so that the bristles directly receive the emitted ultraviolet rays for better sterilization.

The toothbrush handle compartment 214 may include one or more third drain holes 217 for draining moisture that runs down from the toothbrush handle 420 or the toothbrush bristle compartment 212.

Referring to FIG. 4, a holder 280 is provided between the toothbrush bristle and handle compartments 212 and 214 of the storage space 210, for securely holding a stored toothbrush 400.

Referring to FIG. 12, the holder 280 has a holding part 282 respectively elevated on either side thereof and a fixing art 284 below the holding parts 282. A toothbrush handle 420 rests with the inner portions of the holding part 282, and the fixing part 284 is inserted and fixed in a fixing hole 218 formed in the floor of the storage space 210.

The holding part 282 of the holder 280 may form an interior portion that is not perpendicular, but disposed at a tangent that coincides with the angle made by a toothbrush handle 420 held therein, for an improved insertion and holding of the handle.

The holder 280, of course, may be made of pliable rubber or composite material with a degree of elasticity.

In further detail, diagram A of FIG. 12 shows a tangential holder that complies with the angle of the toothbrush handle inserted therein for a secure fit. On the other hand, diagram B shows gaps between a toothbrush and the holding surfaces of a holder when the toothbrush with a tangential handle is placed in the holder.

The cover 300a includes a hinge hole 310 formed at the rear on either side thereof, a plurality of ventilating holes 320 formed on its top surface, and a button 340 protruding at the rear thereof.

Referring to FIG. 8, the cover includes a hooked protrusion 362 extending downward from the central front portion thereof, and a supporting section 364 formed respectively to either side of the hooked protrusion 362. The supporting section 364 may be formed horizontally flush with the lower end of the cover 300a.

Referring to FIGS. 4 through 6, a detachable protective cap 500 is provided in the toothbrush bristle compartment 212 of the upper case 200a. The protective cap 500 is open at the top, and has a second ultraviolet ray emitting hole 510 formed on a side thereof, a plurality of second drain holes 530 and second supports formed on its floor 520, and an open portion 50 on a side thereof for easy insertion of a toothbrush 400.

The second drain holes 530 may be formed vertically in line with the drain holes 216 formed in the toothbrush bristle compartment, and may be countersink-shaped with upper portions formed wider than their lower portions.

The second support may selectively include the same components as the support of the toothbrush bristle compartment 212, which include a ridge 542, a double incline 544, and a single incline 546. In this case, the bottom surface may form portions recessing inward, so that the support of the upper case can be inserted into the recessed portions.

The open portion 550 forms a boundary 560 rising a predetermined distance from the floor 520 to prevent moisture collected on the floor 520 from flowing into the handle compartment 214. The boundary 560 may be formed low enough not to come into contact with the lower surface of a stored toothbrush handle 420.

Referring to FIG. 8, the pivoting member 600 includes a horizontal bar 610 forming an inserting space in its middle 612, a vertical bar 620 extending downward from the bottom of the horizontal bar 610, and a hinge hole 614 formed respectively on either side at the inner junction of the horizontal and vertical bars 610 and 620. The vertical bar 620 has an anti-slip ridge 622 formed at the bottom of its front surface.

Referring to FIG. 13, a transparent window 700 and a reflector 800 are formed on the top surface of the cover 300a.

The transparent window 700 may include a semitransparent material and a hook 710 formed at its bottom. The upper surface of the cover 300a, on which the transparent window 700 is disposed, includes an inserting hole 370 with a supporting ledge 372 formed on its inner periphery. The transparent window 700 is mounted on the supporting ledge 372, and the hook 710 of the transparent window 700 passes through the inserting hole 370 of the cover 300a and hooks on the bottom surface of the supporting ledge 372.

The inserting hole 370 formed on the cover 300a may be formed above the toothbrush bristle compartment 212, so that the light emitted from the sterilizing lamp 162 through the ultraviolet ray emitting hole 240 formed in the toothbrush bristle compartment 212 is visible through the semitransparent material to be aesthetically pleasing.

Also, the reflector 800, which is provided below the transparent window 700, functions as a mirror, and can be made of glass, a compound resin, metal, or various other materials.

The cover 300a may be made entirely of a semitransparent material, and the reflector 800 may be attached to the top surface of the cover 300a for use.

In other words, a portable toothbrush sterilizer 10 includes an upper case 200a with a storage space 210 for a toothbrush 400 formed within that is coupled on top of a lower case 100a with a sterilizer 160 having a sterilizing lamp 162 and a portable battery stored within. The hinge holes 310 of the cover 300a are inserted over the hinge protrusions 130 of the lower case 100a, and the cover 300a pivots around the hinge protrusions 130 to open and close the top of the upper case 200a.

The protective cap 500 is attached to the toothbrush bristle compartment 212 of the upper case 200a, and a pivoting member 600 is inserted and coupled over a pivoting protrusion 264 at the central front portion of the upper case 200a.

Also, a transparent window 700 and a reflector 800 are formed on the top surface of the cover 300a.

Use of the above-structured portable toothbrush sterilizer is described as follows.

First, to open the cover 300a, the pivoting member 600 (as shown in FIGS. 9A and 9B) located at the front of the portable toothbrush sterilizer 10a is pressed.

Here, the anti-slip ridge 622 at the lower portion of the vertical bar 620 on the pivoting member 600 may be pressed, whereupon the pressed pivoting member 600 pivots around the pivoting protrusions 264 to raise the supporting section 364 resting against the top surface of the horizontal bar 610.

Through the raising of the supporting section 364, the hooked protrusion 362 formed in the central portion of the cover 300a is forcefully detached from the hooked tab 262 of the upper case 200a to remove the hooking force. Through this removal of the hooking force, the cover 300a can easily be pivoted and opened.

In this way, the upper case 200a is opened, and a toothbrush 400 stored therein can be removed and used. After use, the toothbrush 400 is returned to the storage space 210 and the cover 300a is closed in the following way.

First, when inserting a toothbrush 400 used by a user into the storage space 210, the toothbrush is inserted into the open portion of the holding part 282 of the holder 280 provided in the storage space 210. Here, the holding part 282 has the same slant as the toothbrush 400 to increase its holding strength of the toothbrush 400.

The toothbrush bristles 410 that are placed in the toothbrush bristle compartment 212 of the storage space 210 are supported by the second supports a predetermined height from the floor 520 of the protective cap 500, so that the moisture on the bristles 410 drain onto the floor 520.

The moisture collected on the floor 520 drain through the second drain holes 530 and the drain holes 216 connected with the second drain holes 530, and drain to the outside through the mounting hole 112 of the lower case 100a.

The moisture that fails to drain through the floor 520 is dried from the heat generated by the sterilizing lamp 162. In the related art, a portion of the moisture flows into the handle compartment 214. Here, however, the boundary 560 on the protective cap 500 prevents moisture from flowing into the handle compartment 214.

After the storing of the toothbrush 400 in the storage space 210 is completed, the cover is pivoted, so that the hooked protrusion 362 of the cover 300a rests on the hooked tab 262. If further pressure is exerted, the supporting section 364 provided on either side of the hooked protrusion 362 presses on the horizontal bar 610 of the pivoting member 600.

The pressed pivoting member 600 pivots around the pivoting protrusion 264 in a direction opposite to the opening direction, and the hooked protrusion 362 inserts through the inserting space 612 of the pivoting member 600 so that its rear portion catches on the hooked tab 262 to complete the closing of the cover 300a.

The button 340 of the closed cover 300a inserts in the switch hole 250 formed at the upper surface 220 or peripheral wall 230 of the upper case 200a to press the touch switch 164 recessed in the switch hole 250.

The sterilizing lamp 162 provided at a side of the sterilizer 160 operates when the touch switch 164 is pressed, to sterilize the toothbrush bristles 410 stored inside the protective cap 500. Because the toothbrush bristles 410 are raised a predetermined height by the second support 520 of the protective cap 500, they are directly aligned to receive the ultraviolet rays emitted from the sterilizing lamp 162, for more effective sterilization.

Because a semi-transparent transparent window 700 and a reflector 700 are provided on the top surface of the closed cover 300a, when the sterilizing lamp 162 illuminates, its semi-transparent glow through the window is visually agreeable.

By adding a detachable protective cap to the toothbrush bristle compartment according to the above-described embodiments of the present invention, the detachable cap allows easy washing of the sterilizer for maintaining cleanliness and preventing discoloration over a long period of use.

Also, by forming a boundary in the open portion of the storage space at the neck of the toothbrush, the boundary prevents moisture collected on the floor of the protective cap from flowing down to the handle compartment to minimize contamination thereof.

Furthermore, by forming a plurality of drain holes on the floors of the upper case and the protective cap, moisture that collects on the floor of the protective cap can quickly drain through the drain holes to the outside, in order to minimize contamination of the floor of the protective cap.

Additionally, the pivoting of a pivoting member can easily unhook a hooked protrusion from a hooked tab to open the cover, in order to facilitate product use.

Thus, the use of separate levering and opening tabs is not required, to improve the outer design of the portable toothbrush sterilizer and therefore improve its competitiveness.

Moreover, because a portion of the touch switch is recessed in the switch hole of the upper case and does not protrude, accidental triggering of the touch switch is prevented. Only when the cover is closed is the touch switch pressed by the button.

Also, by forming at least one ridge for elevating the bristles a predetermined height within the toothbrush bristle compartment, the moisture on the bristles drains quickly to improve sterilizing effectiveness.

Further, by forming a semi-transparent window on the top surface of the cover above the toothbrush bristle compartment and a reflecting mirror below the window, the light emitted from the ultraviolet lamp passes through the semi-transparent window for aesthetic amelioration, and the window provides functionality for a user.

It will be apparent to those skilled in the art that various modifications and variations can be made in the present invention. Thus, it is intended that the present invention covers the modifications and variations of this invention provided they come within the scope of the appended claims and their equivalents.

For example, a plurality of drain holes may be formed on the floor of the lower case to improve draining through the drain holes in the protective cap.

What is claimed is:

1. A portable toothbrush sterilizer comprising:
   a lower case (100a) including a sterilizer compartment (150) for storing a sterilizer (160) having a sterilizing lamp (162) and a touch switch (164), and a battery compartment (140) on a side of the sterilizer compartment (150);
   an upper case (200a) coupled above the lower case (100a) and including:
      a storage space (210) recessed downward from an upper surface (220) of the upper case (200a) for storing a toothbrush (400), the storage space (210) having:
         a toothbrush bristle compartment (212) for storing toothbrush bristles (410) of a toothbrush (400) and having an ultraviolet ray emitting hole (240) formed on a side thereof, and
         a toothbrush handle compartment (214) formed beside the toothbrush bristle compartment (212) for storing a toothbrush handle (420); and
      a switch hole (250) formed on a side of the upper surface (220) or a peripheral wall (230) of the upper case (200a) and having a touch switch (164) inserted and protruding therein;
   a protective cap (500) detachably attached to the toothbrush bristle compartment (212) of the upper case (200a) and including a second ultraviolet ray emitting hole (510) formed at a side thereof, and an open portion (550) formed at another side thereof for allowing storage of the toothbrush handle (420); and
   a pivotably opening and closing cover (300a) disposed above the upper case (200a) and including a button (340) formed on an inner side thereof for pressing the touch switch (164).

2. The portable toothbrush sterilizer of claim 1, wherein the protective cap 500 further includes a floor (520) having one or more of a second support rising a predetermined height from the floor (520).

3. The portable toothbrush sterilizer of claim 2, wherein the second support is a double incline (544) inclining a predetermined height towards either end thereof.

4. The portable toothbrush sterilizer of claim 2, wherein the second support is a single incline (546) declining from a side of the second ultraviolet ray emitting hole (510) to an opposite side.

5. The portable toothbrush sterilizer according to claim 1, wherein the open portion (550) of the protective cap (500) forms a boundary (560) rising a predetermined height from a floor.

6. The portable toothbrush sterilizer according to claim 1, wherein the lower case (100a) further includes a floor (110) having at least one mounting hole (112) formed therein, the storage space (210) of the upper case (200a) has a plurality of drain holes formed therein, and the floor (520) of the protective cap (500) has a plurality of second drain holes (530).

7. The portable toothbrush sterilizer of claim 6, wherein the storage space (210) of the upper case (200a) has a fixing hole (218) formed through a floor thereof, and further comprising a holder (280) with an end thereof inserted and fixed in the fixing hole (218) for allowing easy holding of the toothbrush handle (420), the holder (280) including a holding part (282) formed to rise at either side for forming a central inserting space and having a slant toward one side, and a fixing part (284) formed at a bottom of the holder (280) for inserting and fixing in the fixing hole (218).

8. The portable toothbrush sterilizer according to claim 1, wherein:
   the lower case (100a) includes a hollow portion (124) formed at a front central portion thereof,
   the upper case (200a) includes a hollow portion (232) formed at a front central portion thereof, the hollow portion (232) having a pivoting protrusion (264) respectively protruding from either end thereof and a hooked tab (262) formed therebehind; and
   the cover (300a) includes a hooked protrusion (362) extending downward from a frontal inside center portion thereof for hooking with the hooked tab (262), and a supporting section (364) formed respectively on either side of the hooked protrusion (362),
   the portable toothbrush further comprising: a pivoting member (600) disposed in the hollow portion (124) of the lower case (100a) and the hollow portion (232) of the upper case (200a), and including a horizontal bar (610) having an inserting space 612 formed at a center thereof for preventing interference of the hooked tab (262) and the hooked protrusion (362), a vertical bar (620) vertically disposed at a front of the horizontal bar (610), and a hinge hole (614) formed at either side of the horizontal bar (610) and vertical bar (620) with one side of the hinge hole (614) open for inserting the pivoting protrusion (264) of the upper case (200a) therein.

9. The portable toothbrush sterilizer of claim 8, wherein the cover (300a) is formed partially or entirely of a semi-transparent material.

10. The portable toothbrush sterilizer of claim 8, wherein the cover (300a) includes a reflector (800) formed on an upper surface thereof.

11. The portable toothbrush sterilizer of claim 8, wherein the storage space (210) of the upper case (200a) has a fixing hole (218) formed through a floor thereof, and further comprising a holder (280) with an end thereof inserted and fixed in the fixing hole (218) for allowing easy holding of the toothbrush handle (420), the holder (280) including a holding part (282) formed to rise at either side for forming a central inserting space and having a slant toward one side, and a fixing part (284) formed at a bottom of the holder (280) for inserting and fixing in the fixing hole (218).

12. The portable toothbrush sterilizer of claim 1, wherein the touch switch (164) of the sterilizer (160) is formed in a length that does not protrude from the switch hole (250) of the upper case (200a).

13. The portable toothbrush sterilizer of claim 1, wherein the cover (300a) is formed partially or entirely of a semi-transparent material.

14. The portable toothbrush sterilizer of claim 1, wherein the cover (300a) includes a reflector (800) formed on an upper surface thereof.

15. The portable toothbrush sterilizer of claim 1, wherein the storage space (210) of the upper case (200*a*) has a fixing hole (218) formed through a floor thereof, and further comprising a holder (280) with an end thereof inserted and fixed in the fixing hole (218) for allowing easy holding of the toothbrush handle (420), the holder (280) including a holding part (282) formed to rise at either side for forming a central inserting space and having a slant toward one side, and a fixing part (284) formed at a bottom of the holder (280) for inserting and fixing in the fixing hole (218).

* * * * *